US012224068B2

(12) United States Patent
Ownby et al.

(10) Patent No.: US 12,224,068 B2
(45) Date of Patent: Feb. 11, 2025

(54) ASSESSMENT OF HUMAN COMPREHENSION BY AN AUTOMATED AGENT

(71) Applicants: Nova Southeastern University, Fort Lauderdale, FL (US); Emory University, Atlanta, GA (US)

(72) Inventors: Raymond L. Ownby, Fort Lauderdale, FL (US); Amarilis Acevedo, Fort Lauderdale, FL (US); Drenna Waldrop-Valverde, Atlanta, GA (US)

(73) Assignees: Nova Southeastern University, Fort Lauderdale, FL (US); Emory University, Atlanta, GA (US)

( * ) Notice: Subject to any disclaimer, the term of this patent is extended or adjusted under 35 U.S.C. 154(b) by 1098 days.

(21) Appl. No.: 16/961,266

(22) PCT Filed: Jan. 11, 2019

(86) PCT No.: PCT/US2019/013319
§ 371 (c)(1),
(2) Date: Jul. 10, 2020

(87) PCT Pub. No.: WO2019/140275
PCT Pub. Date: Jul. 18, 2019

(65) Prior Publication Data

US 2021/0065908 A1 Mar. 4, 2021

Related U.S. Application Data

(60) Provisional application No. 62/616,710, filed on Jan. 12, 2018.

(51) Int. Cl.
*G16H 50/30* (2018.01)
*G16H 10/20* (2018.01)
*G16H 10/60* (2018.01)

(52) U.S. Cl.
CPC ............. *G16H 50/30* (2018.01); *G16H 10/20* (2018.01); *G16H 10/60* (2018.01)

(58) Field of Classification Search
USPC ........................................................... 702/19
See application file for complete search history.

(56) References Cited

U.S. PATENT DOCUMENTS

2008/0126123 A1* 5/2008 Duckert ................... G09B 7/00 705/2
2013/0325498 A1* 12/2013 Muza, Jr. ............... G16H 50/30 705/2
2015/0113430 A1* 4/2015 Del Rio ................ G06F 40/151 715/747
2016/0098514 A1 4/2016 Roder et al.
2016/0232805 A1* 8/2016 Gibson .................. G16H 20/10

OTHER PUBLICATIONS

Collins, Sarah A., et al. "Health literacy screening instruments for eHealth applications: a systematic review." Journal of biomedical informatics 45.3 (2012): 598-607. (Year: 2012).*

Wikipedia "Logit." Wikipedia, The Free Encyclopedia. Wikipedia, The Free Encyclopedia, Aug. 6, 2023. Web. Aug. 7, 2023. (Year: 2023).*

Wikipedia "Maximum likelihood estimation." Wikipedia, The Free Encyclopedia. Wikipedia, The Free Encyclopedia, Aug. 2, 2023. Web. Aug. 7, 2023. (Year: 2023).*

Paasche-Orlow, Michael K., et al. "The prevalence of limited health literacy." Journal of general internal medicine 20.2 (2005): 175-184.*

Jarvis, Mary I. "Customization of Multimedia Instruction Template for Low Literates. Effective Communication on Computer-Lessons for Use with New Reading Disk. Workplace Education. Project ALERT." (1997).*

International Search Report and Written Opinion for PCT/US2019/013317 dated Mar. 25, 2019.

Ownby et al., A Mobile App for Chronic Disease Self-Management: Protocol for Randomized Controlled Trail; JMIR Res Protocols. Apr. 2017 6(4); retrieved Aug. 14, 2017.

Ownby et al., Abilities, skills and knowledge in measures of health literacy; Patient Education and Counseling 95 (2014) 211-217.

Ownby et al., Baseline medication adherence and response to an electronically delivered health literacy intervention targeting adherence; Neurobehavioral HIV Medicine Oct. 17, 2012: 4 113-121.

Ownby et al., Cost effectiveness of a computer-delivered intervention to improve HIV medication adherence; BMC Medical Informatics and Decision Making 2013, 13:29.

Ownby et al., Development and initial validation of a computer-administered health literacy assessment in Spanish and English: Flight/Vidas; Patient Related Outcome Measures Aug. 17, 2013: 4 21-35.

McCaffrey et al.; Health literacy in engaging target populations in developing and evaluating health care Interventions; Health Literacy Annual Nov. 3, 2015.

(Continued)

*Primary Examiner* — G. Steven Vanni
(74) *Attorney, Agent, or Firm* — Fleit Intellectual Property Law; Paul D. Bianco; Jon Gibbons

(57) ABSTRACT

An electronic processing system agent accesses population health literacy data from at least 100 individuals pertaining to assessed health literacy of members of the population, and demographic data from the population corresponding to age, race, and education level. The agent collects skills data from the patient corresponding to a set of questions relating to skills needed for understanding therapeutic instructions, and personal data relating to the patient's age, race, and education level. The agent carries out a polytomous logistic regression using the collected population health literacy data, demographic data, skills data, and personal data to assign a health literacy level to the patient corresponding to one of a plurality of groups, and communicates a strategy for the patient corresponding to the patient's assigned health literacy level, in real time, to enable the patient to have a communication of therapeutic instructions when the patient has responded to the set of questions.

14 Claims, 4 Drawing Sheets

(56) References Cited

OTHER PUBLICATIONS

Ownby et al., Patient Centered Health Literacy; Giving people the information they need, when they need it, in a way they can use; Oct. 22, 2018.

Jacobs et al.; A qualitative study examining health literacy and chronic illness self-management in Hispanic and non-Hispanic older adults; Journal of Multidisciplinary Healthcare; Dovepress, Apr. 20, 2017: 10 167-177.

Ownby et al., Quality of life, health status, and health service utilization related to a new measure of health literacy; Flight/Vidas; Patient Education and Counseling 2014.

Ownby et al., Tailored Information and Automated Reminding to Improve Medication Adherence in Spanish- and English-Speaking Elders Treated for Memory Impairment; NIH Public Access Author Manuscript; Clin Gerontol May 1, 2012; 35(3).

IPRP Preliminary Search Report and Written Opinion for PCT/US2019/013317 dated Jul. 23, 2020.

Elizabeth A. Hahn et al., Health Literacy Assessment Using Talking Touchscreen Technology (Health LiTT): A New Item Response Theory-Based Measure of Health Literacy; Journal of Health Communication, 16:150-162, Copyright Taylor & Francis Group, 2011.

Andrew Pleasant et al., Health Literacy Measurement: A Proposed Research Agenda ; Journal of Health Communication, 16:11-21, Copyright #Taylor & Francis Group, 2011.

Ownby et al., A Mobile App for Chronic Disease Self-Management for Individuals with Low Health Literacy: A Multisite Randomized Controlled Clinical Trial; Journal of Ageing and Longevity, 4:51-71, 2024.

Ownby et al., Enhancing the Impact of Mobile Health Literacy Interventions to Reduce Health Disparities, Q Rev Distance Educ, 20(1): 15-34, 2019.

Panzer AM, Kindig DA (editors), Chapter 2: What is Health Literacy?, Health Literacy: A Prescription to End Confusion, Institute of Medicine (US) Committee on Health Literacy, National Academies Press (US), 2004.

* cited by examiner

Sample description.

| | English mean (SD) | Spanish mean (SD) |
|---|---|---|
| N | 161 | 198 |
| Age | 52.5 (173) | 49.8 (15.6) |
| Years of education | 13.6 (23) | 12.4 (2.8) |
| Income | $31,188 | $27,889 |
| SEI[a] | 44.6 (22.4) | 39.2 (20.1) |
| SES factor score[b] | 0.19 (0.80) | -0.14 (0.82) |
| Crystallized[c] | 95.9 (10.6) | 89.6 (9.0) |
| Fluid[d,e] | 10.6 (2.3) | 10.6 (2.7) |
| WJ passage comprehension[c] | 97.4 (11.0) | 94.8 (11.2) |
| WJ applied problems[c] | 97.1 (11.30) | 87.1 (10.4) |
| Health knowledge[d,e] | 8.8 (3.1) | 7.5 (2.6) |
| TOFHLA Reading[f] | 46.4 (4.4) | 43.3 (7.6) |
| TOFHLA Numeracy[f] | 47.8 (2.8) | 43.5 (6.1) |
| | English *N* | Spanish *N* |
| Gender: Men/Women | 70/91 | 81/118 |
| Race: White/Black | 91/70 | 198/0 |

[a] The occupation socioeconomic index ranges from 0 to 100.

[b] Factor score index combining education, income and socioeconomic index with mean of 0 and standard deviation of 1.

[c] This score has a mean of 100 and standard deviation of 15.

[d] Average of scaled scores that each have a mean of 10 and standard deviation of 3.

[e] Raw score on scale with maximum of 15.

[f] Maximum total score for each is 50.

FIG. 1

ASK predictors of TOFHILA Reading scores (combined sample).

| | Model 1: demographics | | | | Model 2: abilities | | | | Model 3: skills | | | | Model 4: knowledge | | | |
|---|---|---|---|---|---|---|---|---|---|---|---|---|---|---|---|---|
| | B | SE | t | p | B | SE | t | p | B | SE | t | p | B | SE | t | p |
| Intercept | 57.80 | 2.69 | 21.51 | **<0.001** | 28.86 | 4.02 | 7.18 | **<0.001** | 26.79 | 4.01 | 6.68 | **<0.001** | 27.83 | 3.98 | 7.00 | **<0.001** |
| Age | -0.09 | 0.02 | -4.59 | **<0.001** | 0.07 | 0.02 | -4.13 | **<0.001** | -0.08 | 0.02 | -4.57 | **<0.001** | -0.09 | 0.02 | -4.93 | **<0.001** |
| SES | 1.93 | 0.33 | 5.85 | **<0.001** | 0.97 | 0.30 | 3.23 | **0.001** | 0.79 | 0.30 | 2.62 | **0.009** | 0.55 | 0.31 | 1.76 | 0.08 |
| Female gender | 0.51 | 0.54 | 0.94 | 0.35 | 1.56 | 0.48 | 3.26 | **0.001** | 1.50 | 0.47 | 3.17 | **0.002** | 1.23 | 0.48 | 2.59 | **0.01** |
| Black race | -3.10 | 0.86 | -3.62 | **<0.001** | -0.93 | 0.77 | -1.21 | 0.23 | -0.96 | 0.76 | -1.27 | 0.21 | -0.72 | 0.75 | -0.96 | 0.34 |
| Spanish language | -3.22 | 0.72 | -4.46 | **<0.001** | -1.17 | 0.67 | -1.74 | 0.08 | -1.40 | 0.67 | -2.10 | **0.04** | -1.23 | 0.66 | -1.86 | 0.06 |
| Crystallized | | | | | 0.16 | 0.03 | 5.30 | **<0.001** | 0.10 | 0.03 | 3.02 | **0.003** | 0.08 | 0.04 | 2.18 | **0.03** |
| Fluid | | | | | 0.56 | 0.11 | 5.06 | **<0.001** | 0.47 | 0.11 | 4.13 | **<0.001** | 0.46 | 0.11 | 4.15 | **<0.001** |
| Reading | | | | | | | | | 0.09 | 0.03 | 3.14 | **0.002** | 0.09 | 0.03 | 2.95 | **0.003** |
| Knowledge | | | | | | | | | | | | | 0.28 | 0.10 | 2.86 | **0.01** |

All values less than 0.05 are bolded.

FIG. 2

ASK predictors of TOFHILA Numeracy scores (combined sample).

| | Model 1: demographics | | | | Model 2: abilities | | | | Model 3: skills | | | | Model 4: knowledge | | | |
|---|---|---|---|---|---|---|---|---|---|---|---|---|---|---|---|---|
| | B | SE | t | p | B | SE | t | p | B | SE | t | p | B | SE | t | p |
| Intercept | 56.31 | 2.89 | 19.48 | **<0.001** | 43.12 | 4.86 | 8.87 | **<0.001** | 38.34 | 5.34 | 7.24 | **<0.001** | 39.40 | 5.33 | 7.40 | **<0.001** |
| Age | -0.04 | 0.02 | -1.72 | 0.09 | -0.03 | 0.02 | -1.28 | 0.20 | -0.03 | 0.02 | -1.29 | 020 | -0.03 | 0.02 | -132 | 0.13 |
| SES | 0.85 | 0.36 | 2.39 | **0.02** | 0.38 | 0.37 | 1.03 | 0.30 | 0.26 | 0.37 | 0.70 | 0.49 | 0.05 | 0.38 | 0.12 | 0.90 |
| Female gender | 0.39 | 0.58 | 0.68 | 0.50 | 0.92 | 0.58 | 1.58 | 0.12 | 1.14 | 0.59 | 1.93 | *0.054* | 0.92 | 0.60 | 1.53 | 0.13 |
| Black race | -1.67 | 0.92 | -1.81 | 0.07 | -0.61 | 0.94 | -0.65 | 0.51 | 0.43 | 0.93 | -0.46 | 0.65 | -0.24 | 0.94 | -0.26 | 0.80 |
| Spanish language | -4.94 | 0.78 | -6.35 | **<0.001** | -4.06 | 0.82 | -4.97 | **<0.001** | -3.49 | 0.86 | -4.05 | **<0.001** | -3.37 | 0.86 | -3.92 | **<0.001** |
| Crystallized | | | | | 0.06 | 0.04 | 1.68 | 0.10 | 0.03 | 0.04 | 0.91 | 0.37 | 0.01 | 0.04 | 0.23 | 0.82 |
| Fluid | | | | | 0.34 | 0.14 | 2.54 | **0.01** | 0.24 | 0.14 | 1.70 | *0.10* | 0.23 | 0.14 | 1.64 | *0.10* |
| Math | | | | | | | | | 0.07 | 0.04 | 1.98 | **0.049** | 0.07 | 0.04 | 2.00 | **0.047** |
| Knowledge | | | | | | | | | | | | | 0.23 | 0.12 | 1.89 | *0.06* |

All values less than 0.05 are bolded and those that are between 0.05 and 0.10 are in italics.

FIG. 3

ASK Predictors of REALM scores (English speakers only).

| | Model 1: demographics | | | | Model 2: abilities | | | | Model 3: skills | | | | Model 4: knowledge | | | |
|---|---|---|---|---|---|---|---|---|---|---|---|---|---|---|---|---|
| | B | SE | t | p | B | SE | t | p | B | SE | t | p | B | SE | t | p |
| Intercept | 64.32 | 3.37 | 19.11 | **<0.001** | 43.62 | 6.17 | 7.06 | **<0.001** | 39.68 | 6.33 | 6.27 | **<0.001** | 41.84 | 5.94 | 7.04 | **<0.001** |
| Age | -0.01 | 0.03 | -0.19 | 0.85 | -0.01 | 0.03 | -0.34 | 0.74 | -0.02 | 0.03 | -0.70 | 0.49 | -0.03 | 0.03 | -1.17 | 0.25 |
| SES | 1.00 | 0.60 | 1.68 | *0.10* | 0.09 | 0.61 | 0.15 | 0.88 | -0.26 | 0.62 | -0.42 | 0.67 | -0.91 | 0.60 | -1.52 | 0.13 |
| Female gender | 2.38 | 0.96 | 2.46 | **0.02** | 2.86 | 0.93 | 3.09 | **0.002** | 2.91 | 0.91 | 3.19 | **0.002** | 2.09 | 0.87 | 2.59 | **0.02** |
| Black race | -3.42 | 1.16 | -2.96 | **<0.001** | -2.61 | 1.17 | -2.23 | **0.03** | -2.65 | 1.15 | -2.30 | **0.02** | -1.88 | 1.09 | -1.72 | *0.09* |
| Crystallized | | | | | 0.21 | 0.06 | 3.51 | **0.001** | 0.12 | 0.07 | 1.79 | *0.08* | 0.05 | 0.07 | 0.78 | 0.44 |
| Fluid | | | | | -0.07 | 0.25 | -0.26 | 0.86 | -0.20 | 0.26 | -0.80 | 0.42 | -0.21 | 0.24 | -0.88 | 0.38 |
| Reading | | | | | | | | | 0.14 | 0.06 | 2.24 | **0.03** | 0.13 | 0.06 | 2.20 | **0.03** |
| Knowledge | | | | | | | | | | | | | 0.79 | 0.18 | 4.45 | **<0.001** |

All values less than 0.05 are bolded and those that are between 0.05 and 0.10 are in italics.

FIG. 4

ASK predictors of SAHLSA scores (Spanish speakers only).

| | Model 1: demographics[a] | | | | Model 2: abilities | | | | Model 3: skills | | | | Model 4: knowledge | | | |
|---|---|---|---|---|---|---|---|---|---|---|---|---|---|---|---|---|
| | B | SE | t | p | B | SE | t | p | B | SE | t | p | B | SE | t | p |
| Intercept | 42.40 | 2.10 | 20.20 | **<0.001** | 29.38 | 6.12 | 4.80 | **<0.001** | 27.17 | 6.25 | 4.35 | **<0.001** | 29.98 | 6.44 | 4.65 | **<0.001** |
| Age | 0.01 | 0.04 | 0.19 | 0.85 | 0.04 | 0.04 | 0.91 | 0.36 | 0.03 | 0.04 | 0.77 | 0.44 | 0.02 | 0.04 | 0.50 | 0.26 |
| SES | 1.42 | 0.55 | 2.58 | **0.01** | 1.19 | 0.57 | 2.09 | **0.04** | 1.06 | 0.57 | 1.86 | *0.07* | 0.76 | 0.60 | 1.27 | 0.21 |
| Female gender | 1.71 | 0.92 | 1.87 | *0.06* | 1.83 | 0.97 | 1.89 | *0.06* | 1.67 | 0.97 | 1.73 | *0.09* | 1.38 | 0.98 | 1.41 | 0.16 |
| Crystallized | | | | | 0.15 | 0.06 | 2.34 | **0.02** | 0.10 | 0.07 | 1.40 | 0.16 | 0.06 | 0.07 | 0.80 | 0.43 |
| Fluid | | | | | -0.15 | 0.20 | -0.73 | 0.47 | -0.24 | 0.21 | -1.16 | 0.25 | -0.24 | 0.21 | -1.16 | 0.25 |
| Reading | | | | | | | | | 0.09 | 0.05 | 1.58 | 0.12 | 0.08 | 0.05 | 1.39 | 0.17 |
| Knowledge | | | | | | | | | | | | | 0.34 | 0.21 | 1.64 | *0.10* |

All values less than 0.05 are bolded and those that are between 0.05 and 0.10 are in italics.

[a] Models do not include race as all Spanish-speaking participants identified themselves as white.

FIG. 5

Percent of variability ($R^2$) attributed to each block and significance for regression models.

| | TOFHLA Reading | p | TOFHLA Numeracy | p | REALM | p | SAHLSA | p |
|---|---|---|---|---|---|---|---|---|
| Demographics | 19 | **<0.001**[a] | 18 | **<0.001**[a] | 17 | **<0.001**[a] | 7 | **0.02**[a] |
| Abilities | 22 | **<0.001**[b] | 3 | **<0.001**[b] | 5 | **0.001**[b] | 3 | **0.10**[b] |
| Skills | 2 | **<0.002**[b] | 0 | **0.21**[b] | 3 | **0.02**[b] | 2 | **0.12**[b] |
| Knowledge | 1 | **<0.005**[b] | 1 | **<0.08**[b] | 5 | **<0.001**[b] | 2 | **0.10**[b] |
| Total | 44 | | 22 | | 34 | | 14 | |

All values less than 0.05 are bolded.

[a] Significance associated with model predictor for this block of variables; complete statistics included in text.

[b] Significance associated in change in model prediction for this block of variables; complete statistics included in text.

FIG. 6

ASSESSMENT OF HUMAN COMPREHENSION BY AN AUTOMATED AGENT

STATEMENT REGARDING FEDERALLY SPONSORED RESEARCH OR DEVELOPMENT

This invention was made with government support under HL096578, MH086491, MD010368, and AG019745 awarded by the National Institutes of Health. The U.S. government has certain rights in the invention.

FIELD OF THE DISCLOSURE

The disclosure relates to a system and method for assessing human comprehension using an automated agent, and more particularly to communicating a therapeutic treatment based upon an assessment of an ability of a patient to comprehend instructions.

BACKGROUND OF THE DISCLOSURE

People who have difficulty understanding or learning about their health-related problems can encounter challenges to obtaining the healthcare they need. Health literacy is key in helping people understand how to become and stay healthy, and those who have low levels of health literacy are aided by communications about their health in a form and content they can understand.

One approach has been to produce patient instruction materials which represent a "universal precautions" approach, in which all information is presented at a level that most individuals can understand. However, there remains a cohort which cannot understand such materials.

A doze procedure (Ackerman, Beier, & Bowen, 2000) assesses reading comprehension, for example testing comprehension by asking the person assessed to supply a word missing in a sentence (e.g., "The sky is ______").

Health literacy has alternatively been defined as "a person's performance on a test of health literacy"; a person's ability to demonstrate that he or she understands health-related information (see Parker, Baker, Williams, & Nurss, 1995); a person's ability to correctly pronounce health-related words (see Murphy, Davis, Long, Jackson, & Decker, 1993); or to identify synonyms of health-related words (see Lee, Bender, Ruiz, & Cho, 2006).

SUMMARY OF THE DISCLOSURE

In an embodiment of the disclosure, a method of automatically evaluating an assessment of a patient's health literacy in order to present therapeutic instructions which are understandable by the patient, comprises using an automated agent having the form of instructions carried out by at least one electronic processor, the automated agent acting to: access population health literacy data from a population of at least 100 individuals pertaining to assessed health literacy of members of the population; access demographic data from the population corresponding to age, race, and level of education; collect skills data from the patient corresponding to a set of questions presented to the patient relating to skills needed for understanding therapeutic instructions; collect personal data relating to the age, race, and level of education of the patient; carry out a polytomous logistic regression using the collected population health literacy data, demographic data, skills data, and personal data in order to assign a health literacy level to the patient corresponding to one of a plurality of groups; and select a communication strategy for the patient corresponding to the assigned health literacy level of the patient, in real time, to enable the patient to have a communication of therapeutic instructions when the patient has responded to the set of questions.

In a variation thereof, the groups correspond to proficient, intermediate, basic, and below basic.

In a further variation thereof, proficient includes individuals who can, at least, independently read text at the high school level; intermediate includes individuals who can, at least, independently read text at an eighth-grade level; basic includes individuals who can, at least, read some basic text; and below basic includes individuals who do not read text at an eighth-grade level.

In a still further variation thereof, communicating therapeutic instructions based upon the assigned health literacy of the individual includes: for a below basic health literacy level, use of at least one of graphics, audio narration, and repetition; for a basic health literacy level, use of single step instructions; for an intermediate health literacy level, use of multi-step instructions; and for a proficient health literacy level, use of complex content in written form.

In other variations thereof, the method further includes performing a binary logistic regression upon the results of the polytomous logistic regression; the binary logistic regression is performed for individuals determined to be at one of two lowest levels assigned for health literacy level groups; the polytomous logistic regression produces a predicted variable which is the natural log of the probability of any individual being a member of one of the groups; the polytomous logistic regression uses a linear combination of an intercept constant and other variables, the variables being weighted so as to provide a composite that is a least-squares solution; and/or the polytomous logistic regression forms a maximum likelihood approach in which the automated agent iteratively derives a solution that is the closest approximation to the actual data while minimizing the second derivative of a function of the model corresponding to a likelihood of the patient being a member of one of the groups.

In additional variations thereof, assignment of a group includes the automated agent calculating the log odds of any group membership for each individual as a linear function of performance on the health literacy measure, age, education, race, and gender; the linear function of performance includes a native language of the patient in addition to age, education, race, and gender; log odd group membership=$\beta0+\beta1\cdot$age+$\beta2\cdot$education+$\beta3\cdot$language+$\beta4\cdot$race+$\beta5\cdot$gender+$\beta6\cdot$health literacy test score, where $\beta i$ refers to numerical values drawn from a statistical output of the polytomous logistic regression; and/or the probabilities of group membership of an individual is further derived by taking the antilog of the result of the polytomous logistic regression and converting the odds into probabilities, with the greatest probability taken as the group membership of the individual.

In still further variations thereof, the health literacy assigned to each member of the population is based upon one or more known health literacy assessment techniques; the known techniques of assessing population health literacy data include at least one of TOFHLA and FN; and/or the set of questions includes not more than 30 questions.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 1 is a description of a sample population of a study in accordance with the disclosure;

FIG. 2 shows ASK predictors of TOFHLA Reading scores in accordance with the disclosure;

FIG. 3 shows ASK predictors of TOFHLA Numeracy scores in accordance with the disclosure;

FIG. 4 shows ASK predictors of REALM scores for English speakers;

FIG. 5 shows ASK predictors of SAHLSA scores for Spanish speakers; and

FIG. 6 shows percent of variability ($R^2$) attributed to each block and significance for regression models.

DETAILED DESCRIPTION OF THE DISCLOSURE

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The inventors have provided certain background of the invention in the following documents which are attached hereto and incorporated by reference herein:

1) The research document entitled "Development and initial validation of a computer administered health literacy assessment in Spanish and English: FLIGHT/VIDAS";
2) The research document entitled "Abilities, skills and knowledge in measures of health literacy";
3) The research document entitled "Quality of life, health status, and health service utilization related to a new measure of health literacy: FLIGHT/VIDAS";
4) The research document entitled "Baseline medication adherence and response to an electronically delivered health literacy intervention targeting adherence";
5) The research document entitled "Cost effectiveness of a computer-delivered intervention to improve HIV medication adherence";
6) The research document entitled "A mobile app for chronic disease self-management: Protocol for a Randomized Controlled Trial";
7) The research document entitled "A qualitative study examining health literacy and chronic illness self-management in Hispanic and non-Hispanic older adults";
8) The research document entitled "Tailored Information and Automated Reminding to Improve Medication Adherence in Spanish- and English-Speaking Elders Treated for Memory Impairment";
9) The FLIGHT/VIDAS User Manual;
10) The presentation entitled "Health literacy in engaging target populations in developing and evaluating health care interventions";
11) The questionnaire entitled "FLIGHT/VIDAS 10 Item Health Literacy Screener Paper and Pencil Version"; and
12) The questionnaire entitled "FLIGHT/VIDAS 20 Item Health Literacy Scale Paper and Pencil Version Response Recording Sheet".

Multiple studies have shown that a large proportion of individuals in the U.S. do not have adequate health literacy to understand and manage their health and interactions with an increasingly complex healthcare system. In contrast, the same individuals are now called upon to take greater responsibility for their health and health care as healthcare providers can spend less and less time providing patients guidance about topics such as medication adverse effects, detection of drug interactions, and behavioral strategies for symptom management and health maintenance.

These issues, as well as the recognition of the potential benefit of informed patients involved in their care, led the authors of the Patient Protection and Affordable Care Act legislation to mandate patient education (e.g., section 2717*a*1B) as part of care delivery. In a similar vein, meaningful use of criteria for electronic health records include "patient-specific education resources" as one of 17 core professional objectives.

These trends in Federal support for healthcare reform create the need for the efficient and effective delivery of health care information both about treatments and health promotion to the public. A typical strategy has been to provide prepared information sheets or pamphlets as a simple intervention that requires little staff time but can make information available. Studies have shown that this strategy, however, has a minimal impact on patient behavior. Many patients do not read the information sheets or pamphlets, and they have been shown to have little impact on patient behavior. The disclosure improves patient compliance, with attendant health benefits, by providing health care information in ways that are tailored to the target audience's personal characteristics.

Developing and adapting patient information resources is time-consuming and requires personnel with expertise in literacy, media, and healthcare. Even if appropriately tailored materials were readily available, providers at the point of care would face the challenge of determining patients' levels of health literacy. This is itself a key problem, as research has shown that providers are unable to judge patients' levels of health literacy and existing assessment techniques require from 20 to 30 minutes of clinician time for administration, scoring, and interpretation. Adequately addressing patients' information needs is difficult or impossible given existing technology, techniques for which have changed little in the past 20 years despite advances in other areas.

In accordance with the disclosure, an automated agent includes a processor that accepts input including information from patients, including age, race, gender, and level of education as well as their performance on a 20-item test of their health literacy. Using weights derived from polytomous logistic regression described elsewhere herein, these individual patient indicators will be combined into a score that allows an automated assignment of the individual according to their needs for health information into one of four groups:

1) Proficient—these are individuals who can independently read text at the high school level and above and make inferences about the text's meaning. Information at this level will be tailored according to preferred language (English or Spanish).
2) Intermediate—individuals at this level can independently read text at an eighth-grade level that expresses clear and concrete concepts. They may need support to make inferences about the ways in which the information provided should be used in caring for themselves.
3) Basic—individuals in this group can read some basic text such as straightforward medication directions, but may have difficulty with more complex issues such as determining when a prescription might have to be refilled. Information is provided in short sentences with supporting graphics and audio narration.
4) Below basic—individuals in this group may be able to recognize the meanings of some words but may not even read simple sentences well. Information is provided with extensive reliance on graphics (e.g., pictures of the sun and moon to indicate when medications can be taken) supplemented by audio narration.

Development of the weights and score is carried out as follows. In a previous NIH-supported project of the inventors, in an extensive and multi-stage development effort, the inventors created a new measure of health literacy. From pilot tests of more than 200 items and a validation study that included about 500 participants (approximately half of whom were Spanish speakers), individuals' performance was studied on a subset of 98 items. The same individuals completed an extensive battery of other measures, allowing them to be precisely characterized as to cognitive function and level of literacy.

The inventors then evaluated subsets of the items according to their qualitative task demands. A scheme was employed for describing the task demands of literacy tasks which was previously developed for several studies sponsored by the US government (e.g., the National Assessment of Adult Literacy done by the National Center for Educational Statistics). These levels, described above, define qualitatively relatively different levels of literacy skills.

Items from the original development study, additionally including known psychometric characteristics such as difficulties for both English and Spanish speakers, were then characterized by the inventors, creating subsets of items with qualitatively different task demands. Items with below basic task demands required, for example, the identification of how many persons were in a picture, or that the person responding accurately add two single-digit numbers. Table 1 presents an example of literacy assessments comparing the National Assessment of Adult Literacy (NAAL) and the F/V method of the disclosure.

TABLE 1

Literacy Assessment Types - Example Comparison of NAAL and F/V

| NAAL | F/V |
|---|---|
| Below Basic | |
| Sign your name on a social security card (96%) | How many missing from a picture (98%) |
| Basic | |
| Fill out a bank deposit slip, adding two numbers (83%) | Add two amounts of carbohydrates managing diabetes (82%) |

TABLE 1-continued

Literacy Assessment Types - Example Comparison of NAAL and F/V

| NAAL | F/V |
|---|---|
| Intermediate | |
| Find three good sources of vitamin E in a nutrient table (66%) | Read a paragraph with multiple facts and extract the cause of the disease discussed (63%) |
| Proficient | |
| Explain the differences between two types of job-related benefits (42%) | Compare values of brand name and generic medicines that vary in dosing frequency and package quantity (56%) |

Table 2 illustrates various communication strategies which may be used based upon health assessment abilities.

TABLE 2

| Examples of Communication Strategy |
|---|
| Below Basic: Heavy emphasis on graphics, audio narration, repetition of information and double checking understanding. |
| Basic: Can understand straightforward instructions such as "take one pill a day" but may have difficulty understanding more complex prose and quantitative tasks. Avoid complex or multi-step instructions. Universal precautions materials may work. |
| Intermediate: Can understand moderately complex directions, but may not be able to extract relevant facts from those that compete (e.g., a news story). Understanding of probability is only fair, and can only do fairly simple arithmetic tasks. |
| Proficient: Can understand complex directions, and can extract relevant information from complex and confusing content. May want significantly more information, but can consume it in written form. |

Participants' performance on each of these subsets of items are used to define groups of individuals with qualitatively different health literacy skills using latent class analysis. Individuals with below basic health literacy skills, for example, performed adequately on the subset of items that required below basic skills but less well on items with more complex task demands. Only those individuals with the highest levels of health literacy performed well on each of the items subsets.

Each individual in the validation study was then assigned to one of the groups derived from the latent class analysis using polytomous logistic regression. The accuracy of classification of individuals in these groups based on their total scores to the best 20 items from the health literacy measure was then assessed. A model that also included participants' age, education, gender, and race was also evaluated. The combination of personal characteristics and health literacy scale performance provided the most accurate classification of individuals, and can therefore be used as the basis for tailoring information to individuals' likely health literacy requirements.

Tailored information means providing information in a way that is relevant to the person based on: Perceived need (What I want to know); Gender; Race; Language; Level of health literacy, and age. There is a need to need to match content with recipients' abilities. The problem with tailoring is that it can be difficult to produce tailored information, and would be too time consuming to carry out for individuals, but the assignment of patients to specific groups based on latent class analysis and logistic regression in accordance with the disclosure can be carried out in a timely manner by a robotic entity.

Certain aspects of the foregoing can be outlined as follows. Tailored information messages include information that is modified to be specifically relevant to the intended recipient. The inventors have found that such tailored messages are more effective in modifying behavior than messages that are not tailored. Providing health care information to patients is an increasingly important function of health care organizations, at least because it is part of mandated functions under federal criteria for meaningful use of electronic health records (Stage 1 criteria, July 2014), as well as addressing the need for patients to become more actively engaged in their own care. Stage 2 meaningful use criteria will require that providers identify patient-specific educational resources and provide them to patients, which is also addressed by the disclosure.

Large Electronic Health Record (EHR) providers have developed methods to provide patient education as part of their services, but based on online information, these methods are simply to allow providers to print out the equivalent of a simple handout. Studies of the effects of simply providing similar handouts to patients have shown that they are minimally effective, especially when compared to tailored information. Evaluation of example handouts, however, show that they also are written in language that makes them difficult or impossible for many patients with low health literacy to understand.

The disclosure addresses this critical failing by using a brief assessment of patients' health literacy to determine the appropriate strategy to deliver messages to them about their health care. Patients who read very slowly, for example, have told the inventors they appreciate information provided to them with supplementary audio narration. Patients with even lower reading skills, who may understand very little written information, can benefit from the supplementation of text information with graphics as well as audio narration. Conversely, individuals with higher levels of reading or mathematics skills may not need such substantial modifications of information presentation yet still benefit from learning specific factual knowledge about their health conditions and treatment. Information that is provided at a level appropriate for the patient is more acceptable to the patient, more readily understood, and significantly more likely to result in behavior change. The inventors have assessed research participants' reaction to a system embodying the disclosure, and have observed a positive reaction that spans age, race, level of reading skill, and level of technological experience.

Moreover, the inventors have found that those with lowest level of disease-related information and socially disadvantaged backgrounds rated the system more positively than people with higher levels of information and more advantaged backgrounds. In addition to the social benefit of the system, socially disadvantaged patients are attractive targets for intervention as they are often those most costly to health care systems through frequent use of emergency departments, readmissions after hospital discharge, and low levels of adherence to treatment recommendations.

The disclosure thus addresses a critically important and unmet need of health care organizations—to address meaningful use criteria and improve patient outcomes. The disclosure can readily be implemented through integration into existing EHR systems. In a future payer system in which payments are based on performance rather than on service delivery, an automated system for information delivery that is linked to methods proven to improve treatment adherence is likely to have substantial financial benefits for provider organizations.

Identifying individuals with low health literacy in order to provide appropriate health information has been a central goal of health literacy assessment. Although score cutoffs on several measures have been provided to identify people with low health literacy, most are not based on objective criteria and studies have shown low levels of agreement among measures. In a related study, the inventors identified groups of persons with various levels of health literacy based on their responses to different types of health literacy tasks. The disclosure correlates a variety of predictors, including age, education, race, gender, language, and performance on several health literacy tests, to identify individuals with specific types of information needs.

The disclosure uses data from studies of the inventors to develop a measure of health literacy, including Fostering Literacy for Good Health Today/Vive Desarollando Amplia Salud, or FLIGHT/VIDAS. In the studies, previously identified subgroups of individuals with levels of health literacy at below basic, basic, intermediate, and proficient levels based on their performance on test items were classified on the basis of the complexity of their task demands.

The incorporated references detail questions and tests which can be presented to patients in order to obtain raw data pertaining to health literacy, or an ability to understand instructions relating to following a therapeutic course of treatment that has been prescribed for the patient by health care professionals. In accordance with the disclosure, multinomial and binomial logistic regression models are used to assess the ability of the statistical models described in the incorporated references to predict group membership for each patient. Predictors include demographic variables and level of education to identify individuals with specific levels of health literacy. Models include participants' performance on the Tests of Functional Health Literacy in Adults (TOFHLA) and FLIGHT/VIDAS (F/V) 20-item scale. An ability is assessed for each model's ability to predict group membership in one of the four groups of age, education, race, and gender, and in a binary classification of below basic/basic vs. intermediate/proficient. While a test including 10 to 20 items has been found to be statistically sufficient, and advantageous in terms of a brief testing duration, a longer test of 30, 40, or 50 items can alternatively be carried out in accordance with the disclosure.

In such tests, the testing sample included 493 individuals, with 243 English and 250 Spanish speaking; 188 men and 305 women; and with ages ranging from 18 to 93 with a mean age of 53.2 years. Fifty-nine test participants were in the below basic group, with 132 in the basic, 153 in the intermediate, and 144 in the proficient group. A model including demographic variables and education significantly predicted group membership ($p<0.001$; pseudo $R2=0.48$; 53% correctly classified). The addition of the TOFHLA or F/V scores improved classification. For the model using the TOHFLA total score, ($p<0.001$; pseudo $R2=0.60$; 59% correctly classified). The model using the F/V 20-item scale score ($p<0.001$; pseudo $R2=0.86$; 79% correctly classified). Both measures were able to correctly classify whether individuals had basic or below basic compared to intermediate or proficient levels of health literacy (TOFHLA pseudo $R2=0.61$, 81% correct; F/V pseudo $R2=0.91$, 95% correct). In accordance with the disclosure, it is advantageous to collect data from a testing sample of at least 100 individuals, with greater accuracy advantageously obtained from a diverse population of at least 300 individuals.

Accordingly, the algorithm of the disclosure includes individuals' personal characteristics as well as other factors better reflects their potential performance on a measure of health literacy, and performs substantially better at identifying individuals with specific levels of health literacy. The inclusion of both elements is substantially better than either element alone. With minimal additional data collection combined with assessment of health literacy, the algorithms of the disclosure could be used to more efficiently identify individuals with specific information needs for health information communication.

In an embodiment, scores on each of a series of subscales, representing the number of correct responses to health literacy questions, were calculated for each of the 497 participants in a study by the inventors, which was used to create a classification method.

Latent class analysis (LCA; also known as latent profile analysis) is a statistical technique whereby individuals can be assigned to categories based on attributes used by the classification program. We used the LCA routine in MPlus statistical software to identify classes in the aforedescribed data. The number of classes was determined by evaluation of the information criteria (Bayesian Information Criteria, or BIC) and the Vuong-Lo-Mendell-Rubin Likelihood Ratio Test. The optimal solution yielded the four afore-described classes of individuals as defined by their performance on the four qualitatively different types of health literacy tasks. The median number of items on each subscale answered correctly for each of the classes of individuals was then calculated and plotted (see FIG. 1). The performance of the four groups varied widely with respect to the type of health literacy task. One group (purple line) performed only moderately well on even the items requiring below basic skills. Another group performed much better on items requiring below basic skills but only moderately well on basic items and relatively poorly on intermediate and proficient items. The other two groups thus perform in ways consistent with better performance on items of increasing complexity. The LCA results were then also validated by examining their relations with three other well-known measures of health literacy and a widely-used standardized test of reading comprehension used as a diagnostic gold standard in our study. In all analyses, performance on these measures was significantly related to group membership.

To carry out the disclosure, a polytomous logistic regression model uses participants' performance on the 10-item health literacy screening measure as well as age, gender, race, language, and education. This model was validated in multiple random subsamples. For these validation analyses, the software utilized was instructed to draw a random sample of cases from all cases and repeat the analysis. This process is done repeatedly in order to provide a statistically valid estimate of how the model would perform in other instances such as in another group of persons. This procedure, repeated with 5,000 iterations, yields an estimate of the average performance of the model as well as a probabilistic estimate of the likely range of accuracies for future estimates. In all instances, between 68 and 73% of individuals were correctly classified. The inventors observed that many of the misclassifications were between the Below Basic and Basic groups or between the Intermediate and Proficient groups. A binary logistic regression model was therefore evaluated for classification of individuals into two groups (Below Basic combined with Basic or Intermediate combined with Proficient). The model was 93% accurate in these analyses. It is therefore concluded that by using the disclosure it is possible to identify individuals with specific information delivery needs in a highly accurate fashion.

The usefulness of this procedure lies in the ability to identify individuals with low levels of health literacy. For them to adequately understand information that is presented to them either in writing or orally, they will likely benefit from a presentation that uses simple vocabulary, short sentences, and is supplemented with explanatory graphics and audio narration. Individuals with higher levels of health literacy may be able to benefit from text-only materials, although it is likely that they should be tailored to make them personally relevant to the intended recipient. As research studies have shown that tailored information is much more likely to have an effect on behavior.

In practice, the ten-item measure can easily be deployed on the Web and readily integrated into an electronic health record. It is self-scoring and with minimal programming of the EHR, a patient's score can be recorded in his or her record and transmitted to a provider. This score can also be used to automatically tailor information provided to the patient by the provider in compliance with meaningful use criteria. As insurer payments move away from a model of paying for service delivery toward pay for performance (objective improvement in patient health; prevention of disease and related costs) the ability of an information intervention to enhance patient outcomes will be economically relevant. Beyond improved performance and health, implementation of the disclosure, costs of deployment of the disclosure can be offset by savings resulting from changes in patient behavior that shifts from inpatient to outpatient utilization of services.

The algorithm uses ordinary polytomous logistic regression. This model is based on the classic linear regression model in which a predicted outcome variable is modeled as a linear combination of a constant (also called an intercept) and other variables weighted so as to provide a composite that minimizes the squared errors of its prediction of the actual values in data (also known as least-squares solution). At its base, this approach is modified in polytomous logistics regression analysis so that the predicted variable is now the natural log of the probability of any individual being a member of one of the groups. In practice, the device will model the probability of group membership compared to a reference group, in this case those individuals considered to have proficient health literacy skills. It may be noted that the actual calculation approach used in modern statistical analysis packages (widely available commercially and as open-source software) does not use a least-squares algorithm but rather takes a maximum likelihood approach in which the computational software iteratively derives a solution that is the closest approximation to the actual data while minimizing the second derivative of a function of the model referred to as the likelihood.

Determination of group membership thus utilizes this approach to calculate the log odds of any group membership for each individual as a linear function of performance on the health literacy measure, age, education, race, gender, and language (Spanish or English):

Log odd group membership $=\beta_0+\beta_1\cdot$age$+\beta_2\cdot$education$+\beta_3\cdot$language$+\beta_4\cdot$race$+\beta_5\cdot$gender$+\beta_6\cdot$health literacy test score, where $\beta_i$ refers to numerical values draw from statistical output of the analysis.

Actual probabilities of group membership can then be readily derived by taking the antilog of the result and converting the odds into probabilities. The greatest probability is then taken as the individual's group membership.

The automated agent uses the specific foregoing approach to synthesize inputs from many patients, and to determine a comprehension level or health literary assessment for a specific patient in real time, in an approach which is not only not uniquely and narrowly tailored to this specific automated task, but which would otherwise be computationally infeasible without the automated agent. The health literacy assessment must be performed very quickly, in order to be practical and feasibly carried out within the patient's available time and attention span. Additionally, the analysis with respect to other patients must be complete in real time, in order that the patient can be given appropriate oral, written, or visual instructions at the time of evaluation and presentation of a therapeutic regimen, device, or medicament. The automated agent interfaces with automated data collection devices and human interface devices to capture patient data, and generates the real time analysis for all patients, and for the individual patient, and produces the instruction set which can be read to, or presented to, the individual patient, as soon as a therapy has been determined. All of the foregoing can be carried out without human intervention, analysis, or presentation.

In an embodiment, the instant disclosure can be implemented on a smartphone, tablet, or other portable computing device commonly used by patients. In this embodiment, the disclosure can be combined with and/or implemented using educational and interactive software, such as ADOBE CAPTIVATE, ISPRING, LECTORIS, and CAMTASIA, to facilitate more rapid development, and to provide formats that are easily published and used. The disclosure can additionally be implemented using not only a touch screen interface, but can further use the audio interface to allow participants to hear all items as they are presented.

Additional Example 1

Participants completed a battery of general intellectual, academic skills, and health literacy measures. Demographics Participant age, education, occupation, income, gender, and race were recorded. Principal factor analysis was used to construct a composite index of socioeconomic status based on education, income, and occupational prestige index. The index was constructed to address the limitations of single-indicator measures, as single indicators such as education, income, and occupational status are only moderately correlated and only partially represent an individual's status. The index was calculated by including education, occupational prestige, and income in a principal factor analysis. Each indicator's loading on a single factor (0.27, 0.27, and 0.16 for education, occupational status, and income, respectively) provided weights for calculation of factor scores for each participant.

General intellectual ability can be defined as reflecting a person's acquired knowledge and communication ability (crystallized ability) and capacity to reason and solve novel problems (fluid ability). Crystallized general cognitive abilities were assessed using the Verbal Composite score of the Woodcock-Johnson Psycho-Educational Battery for English speakers and the Woodcock-Muñoz Psycho-Educational Battery for Spanish speakers (WJPEB/WMPEB). These measures tap word knowledge, general information, and verbal reasoning in a series of tasks that yields a single score. Fluid general cognitive abilities were assessed with the Block Design and Matrix Reasoning subtests of the Wechsler Adult Intelligence Scale, Third Edition; the average of these subtests' age-corrected scores yielded an index.

Reading and mathematics skills were assessed with the Passage Comprehension and Applied Problems subtests of WJPEB/WMPEB. The Passage Comprehension subtests use items based on one or two sentences to evaluate reading comprehension. The Applied Problems subtests assess mathematics skill through items requiring problem solving as well as calculation.

Health knowledge was assessed with a subscale of the new measure developed during the study. We developed a brief measure of general health knowledge, which comprised 15 questions, all of knowledge of a specific fact, such as a disease risk factor or a specific drug treatment for a disease, and did not require substantial reading or numeracy skills. For example, "Cholesterol is measured with a . . . ". Other items assessed a broad range of health-related facts, including the part of the body most commonly treated by a specific medical profession (nephrology), what common over-the-counter medications are used for (aspirin for heart attack), and the meaning of blood lipid indices (e.g., HDL).

The health knowledge scale was developed in two stages. A group of candidate items was first administered to older and younger Spanish or English speaking individuals. Preliminary analyses of item performance in both languages and of item discrimination and difficulty allowed us to choose items for the second phase of the study. In this phase, scale items were administered along with the additional measures as described here. The dimensional structure of the new knowledge scale as well as item difficulties were supported through psychometric analyses, although its marginally acceptable internal reliability (Cronbach's alpha=0.67) limits its use to research.

All participants completed either the Spanish or English versions of the Test of Functional Health Literacy in Adults (TOFHLA). English-speakers completed the Rapid Estimate of Adult Literacy in Medicine (REALM), while Spanish speakers completed the Short Assessment of Health Literacy for Spanish-speaking Adults (SAHLSA).

Linear regression models using progressively more complex blocks of variables representing, first, demographics and then the elements of the ASK model were created to assess study hypotheses. Variable blocks after correcting for demographics were evaluated in a logical order from the most general and basic (core intellectual abilities) through the more specific skills acquired early in life (reading or mathematics) to the most specific (health-related knowledge). Models assessed the relative contribution of each element to prediction of each measure. Analyses were completed using SPSS version 21 (Montauk, NY: IBM).

Descriptive statistics for the sample are presented in FIG. 1. Our sample intentionally included participants from a wide range of ages (18-85) and the mean age for the combined sample was 51.0 years (standard deviation==16.5). The sample included individuals with a wide range of education (3-20 years) with a combined sample mean of 12.9 years (standard deviation=2.6).

Regression models are presented in FIGS. 2-5. Results for the TOFHLA Reading subtest (FIG. 2) show that in the model only including demographic variables (Model 1), SES was related to higher scores on the TOFHLA Reading while age, being black, and speaking Spanish were related to lower scores (Model 1 $R^2=0.19$, F=[df=5, 278]=13.32, $p<0.001$). Both crystallized and fluid abilities added to the model's prediction of TOFHLA scores (Model 2 $R^2=0.41$, F for change=[df=2, 276]=49.11, $p<0.001$), while reading added still further to the model ($R^2=0.43$, F for change=[df=1, 275]=9.86, p=0.002), as did health knowledge ($R^2=0.44$, F for change=[df=1, 274]=8.20, p=0.005).

The model for the TOFHLA Numeracy subtest (FIG. 3) also showed that SES was positively and Spanish language was inversely related to scores ($R^2=0.18$, F=[df=5, 279]=12.53, $p<0.001$). The addition of general cognitive abilities increased prediction ($R^2$=0.21, F for change=[df=2,2,277]=8.36, p<0.001). The addition of math skills did not improve prediction ($R^2$=0.21, F for change=[df=1, 276]=1.60, p=0.21) even though it was related to the Numeracy subscale (FIG. 5). Addition of health knowledge to the model did not improve prediction ($R^2$=0.22, F for change=[df=1, 275]=3.17, p=0.08).

The model for English speakers on the REALM is presented in FIG. 4. In Model 1, female gender was positively and black race was inversely related to scores. ($R^2$=0.17, F=[df=4, 134]=6.62, p<0.001). The addition of general cognitive abilities improved prediction ($R^2$=0.25, F for change=[df=2, 132]=7.88, p=0.001), as did the addition of reading ($R^2$=0.28, F for change=[df=1, 131]=5.03, p=0.02), and knowledge ($R^2$=0.34, F for change=[df=1, 130]=19.77, p<0.0001).

The model for the SAHLSA is presented in FIG. 5. In Model 1, only SES was associated with better scores although the value for female gender approached statistical significance ($R^2$=0.07, F model=[df=3, 142]=3.42, p=0.02). The addition of crystallized and fluid abilities did not improve prediction ($R^2$=0.10, F for change=[df=2, 140]=2.81, p=0.06) although crystallized abilities were a significant predictor. Neither the addition of academic reading ($R^2$=0.12 F for change=[df=1,139]=2.51, p=0.12) nor knowledge ($R^2$=0.14, F for change=[df=1, 139]=2.69, p=0.10) increased prediction.

FIG. 6 presents a summary of the variability ($R^2$) accounted for by each block and the significance of change associated with each. The percentage of variability related to demographic variables was similar for the TOFHLA subtests and the REALM while the SAHLSA was less strongly related to demographic variables. TOFHLA Reading scores were significantly related to cognitive abilities, while scores on the other measures were much less clearly related to cognition. Academic skills provided similar contributions in each model, except for the TOFHLA Numeracy subtest which, while a significant predictor, did not improve overall model prediction. In most models, health knowledge provided a small but significant contribution.

Additional Example 2

The inventors used data from a study of a computer-administered health literacy measure with 280 adults 50 years of age or older (mean age 66; 180 women; 227 white and 53 black; 141 English- and 139 Spanish-speaking). Using latent profile analysis, in accordance with the disclosure, of their performance on questions that varied in their cognitive demand characteristics, we identified individuals likely to benefit from specific tailored interventions for chronic disease self-management, such as low literacy text and audio narration. Predictive analytic models (polytomous logistic regression) using demographic variables (age, gender, race, education, and language) and performance on a 10-item health literacy screen were used to identify individuals at one of four functional literacy levels (below basic, basic, intermediate, or proficient).

The model predicting membership in one of the four levels had an accuracy of 74%. For the difference between those with below basic and basic compared to higher levels, the accuracy was much higher (93%; pseudo R2=0.85).

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method of automatically evaluating an assessment of a patient's health literacy in order to present therapeutic instructions which are understandable by the patient, comprising:

using an automated agent having a form of instructions carried out by at least one electronic processor, the automated agent acting to:

access health literacy data from members of a population of at least 100 individuals, wherein the health literacy data indicates that members of the population understand health-related information and health-related words;

access demographic data from the members of the population corresponding to age, race, and level of education;

collect skills data from the patient corresponding to a set of questions presented to the patient relating to skills needed for understanding therapeutic instructions;

collect personal data relating to the age, race, and level of education of the patient;

assign a health literacy level to the patient using a polytomous logistic regression with i) the health literacy of members of the population, ii) the demographic data of members of the population, iii) the skills data of the patient, and iv) the personal data of the patient, wherein the health literacy level is one of a plurality of groups based upon the abilities, skills and knowledge (ASK) predictors of Tests of Functional Health Literacy in Adults (TOFHLA), wherein the plurality of groups include;

proficient includes individuals who can, at least, independently read text at a high school level;

intermediate includes individuals who can, at least, independently read text at an eighth-grade level;

basic includes individuals who can, at least, read sentences below the eighth-grade level; and below basic includes individuals who can read words but cannot understand sentences; and select a communication strategy for the patient corresponding to the assigned health literacy level of the patient, by a computer, to enable the patient to have a communication of therapeutic instructions when the patient has responded to the set of questions, wherein the communication of therapeutic instructions is based upon the assigned health literacy of the patient to include:

for a below basic health literacy level, use of at least one of graphics, audio narration, and repetition;

for a basic health literacy level, use of single step instructions with text in sentences below a reading competence of the eighth-grade level;

for an intermediate health literacy level, use of multi-step instructions; and for a proficient health literacy level, use of multi-step instructions and additional content in written form.

2. The method of claim 1, further comprising:

communicating to the patient, by the automated agent, the therapeutic instructions based on the health literacy level.

3. The method of claim 1, further including performing a binary logistic regression upon results of the polytomous logistic regression.

4. The method of claim 3, wherein the binary logistic regression is performed for individuals determined to be at one of two lowest levels assigned for health literacy level groups.

5. The method of claim 1, wherein the polytomous logistic regression produces a predicted variable which is a natural log of a probability of any individual being a member of one of the groups.

6. The method of claim 1, wherein the polytomous logistic regression uses a linear combination of an intercept constant and other variables, the variables being weighted so as to provide a composite that is a least-squares solution.

7. The method of claim 1, wherein the polytomous logistic regression forms a maximum likelihood approach in which the automated agent iteratively derives a solution that is a closest approximation to an actual data while minimizing a second derivative of a function of a model corresponding to a likelihood of the patient being a member of one of the groups.

8. The method of claim 1, wherein the assignment of a group includes the automated agent calculating log odds of any group membership for each individual as a linear function of performance on the health literacy using the measures of age, education, race, and gender.

9. The method of claim 8, wherein the linear function of performance includes a native language of the patient in addition to age, education, race, and gender.

10. The method of claim 9, wherein log odds group membership-$\beta_0+\beta_1\cdot$age$+\beta_2\cdot$education$+\beta_3\cdot$language$+\beta_4\cdot$race$+\beta_5\cdot$gender$+\beta_6\cdot$health literacy test score, where $\beta_i$ refers to numerical values drawn from a statistical output of the polytomous logistic regression.

11. The method of claim 1, wherein a probability of group membership of an individual is further derived by taking an antilog of a result of the polytomous logistic regression and converting odds into probabilities, with the greatest probability taken as the group membership of the individual.

12. The method of claim 1, wherein the health literacy assigned to each member of the population is based upon one or more known health literacy assessment techniques.

13. The method of claim 12, wherein the known techniques of assessing population health literacy data include at least one of Tests of Functional Health Literacy in Adults (TOFHLA) and FLIGHT/VIDAS (F/V).

14. The method of claim 1, wherein the set of questions includes not more than 30 questions.

* * * * *